(12) United States Patent
Johnson (10) Patent No.: US 12,311,184 B2
(45) Date of Patent: May 27, 2025

(54) METHOD AND USER INTERFACE FOR MANAGING DUTY-CYCLED ELECTRICAL NERVE STIMULATION

(71) Applicant: Medtronic, Inc., Minneapolis, MN (US)

(72) Inventor: Nathan I. Johnson, Saint Paul, MN (US)

(73) Assignee: Medtronic, Inc., Minneapolis, MN (US)

( * ) Notice: Subject to any disclaimer, the term of this patent is extended or adjusted under 35 U.S.C. 154(b) by 58 days.

(21) Appl. No.: 17/516,921

(22) Filed: Nov. 2, 2021

(65) Prior Publication Data

US 2022/0134118 A1    May 5, 2022

Related U.S. Application Data

(60) Provisional application No. 63/198,663, filed on Nov. 2, 2020.

(51) Int. Cl.
    *A61N 1/372*      (2006.01)
    *A61N 1/36*      (2006.01)

(52) U.S. Cl.
    CPC ..... *A61N 1/37247* (2013.01); *A61N 1/36007* (2013.01); *A61N 1/36192* (2013.01); *A61N 1/37282* (2013.01)

(58) Field of Classification Search
    CPC ............ A61N 1/37247; A61N 1/36007; A61N 1/36192; A61N 1/37282; A61N 1/37235; A61N 1/37252; A61N 1/36132; A61N 1/36135; A61N 1/37264
See application file for complete search history.

(56) References Cited

U.S. PATENT DOCUMENTS

| | | | |
|---|---|---|---|
| 7,369,894 B2 | 5/2008 | Gerber |
| 8,204,597 B2 | 6/2012 | Gerber et al. |
| 8,874,217 B2 | 10/2014 | Alataris et al. |
| 8,989,861 B2 | 3/2015 | Su et al. |

(Continued)

FOREIGN PATENT DOCUMENTS

| | | |
|---|---|---|
| EP | 3473294 | 4/2019 |
| WO | WO 2000/001320 | 1/2000 |

(Continued)

OTHER PUBLICATIONS

Amend, Bastian et al. "How Does Sacral Modulation Work Best? Placement and Programming Techniques to Maximize Efficacy", Curr Urol Rep (2011) 12:327-335.

(Continued)

*Primary Examiner* — Mallika D Fairchild
(74) *Attorney, Agent, or Firm* — Husch Blackwell LLP (57) ABSTRACT

An implantable neurostimulation system including an implantable neurostimulation device having one or more electrodes configured to deliver electrical energy to a patient according to a prescribed dosing pattern for the treatment of one or more physiological conditions and an external programmer configured to wirelessly communicate with the implantable neurostimulation device, the external programmer including a user interface enabling a clinician to define an irregular dosing pattern, such that a dose pattern during each day of a calendar month is individually programmable.

10 Claims, 7 Drawing Sheets

(56) References Cited

U.S. PATENT DOCUMENTS

| | | |
|---|---|---|
| 9,272,140 B2 | 3/2016 | Gerber |
| 9,555,246 B2 | 1/2017 | Jiang et al. |
| 9,561,372 B2 | 2/2017 | Jiang et al. |
| 9,956,404 B2 | 5/2018 | Brink et al. |
| 10,029,102 B2 | 7/2018 | Doan et al. |
| 10,299,987 B2 | 5/2019 | Greiner et al. |
| 10,312,031 B2 | 6/2019 | Scherer |
| 10,569,088 B2 | 2/2020 | Dinsmoor et al. |
| 10,576,293 B2 | 3/2020 | Peterson et al. |
| 10,729,903 B2 | 8/2020 | Jiang et al. |
| 11,045,649 B2 | 6/2021 | Wei et al. |
| 2003/0158583 A1 | 8/2003 | Burnett et al. |
| 2004/0193228 A1 | 9/2004 | Gerber |
| 2007/0100388 A1 | 5/2007 | Gerber |
| 2008/0300449 A1 | 12/2008 | Gerber et al. |
| 2010/0185183 A1* | 7/2010 | Alme ............... A61M 5/14276 604/891.1 |
| 2011/0071589 A1 | 3/2011 | Starkebaum et al. |
| 2012/0143286 A1* | 6/2012 | Hahn ............... A61N 1/36185 607/2 |
| 2012/0197338 A1 | 8/2012 | Su et al. |
| 2013/0079840 A1 | 3/2013 | Su et al. |
| 2014/0364920 A1 | 12/2014 | Doan et al. |
| 2016/0045724 A1 | 2/2016 | Lee et al. |
| 2016/0045747 A1 | 2/2016 | Jiang et al. |
| 2016/0136420 A1 | 5/2016 | Brink et al. |
| 2017/0065821 A1 | 3/2017 | Brink et al. |
| 2017/0173328 A1* | 6/2017 | Ostroff ............... A61N 1/3606 |
| 2017/0239470 A1 | 8/2017 | Wei et al. |
| 2018/0133484 A1 | 5/2018 | Dinsmoor et al. |
| 2018/0154144 A1 | 6/2018 | Brink et al. |
| 2018/0289965 A1 | 10/2018 | Nelson et al. |
| 2019/0001139 A1 | 1/2019 | Mishra et al. |
| 2019/0060647 A1 | 2/2019 | Su et al. |
| 2019/0126039 A1* | 5/2019 | Yoo ............... A61N 1/36007 |
| 2019/0217092 A1 | 7/2019 | Baynham et al. |
| 2019/0255331 A1 | 8/2019 | Subbaroyan |
| 2020/0046974 A1 | 2/2020 | Ostroff et al. |
| 2021/0031032 A1 | 2/2021 | Zirpel et al. |
| 2021/0031033 A1 | 2/2021 | Davies et al. |

FOREIGN PATENT DOCUMENTS

| | | |
|---|---|---|
| WO | WO 2000/019939 | 4/2000 |
| WO | WO 2003/026738 | 4/2003 |
| WO | WO 2007/098202 | 8/2007 |
| WO | WO 2011/156288 | 12/2011 |
| WO | WO 2016/028608 | 2/2016 |
| WO | WO 2017/142948 | 8/2017 |

OTHER PUBLICATIONS

Markle Price, Danielle, et al. Abstract of "Prospective Randomized Crossover Trial Comparing Continuous and Cyclic Stimulation in Interstim Therapy", Female Pelvic Med Reconstr Surg. Nov.-Dec. 2015;21(6):355-8.

Cadish, Lauren et al. "Stimulation Latency and Comparison of Cycling Regimens in Women Using Sacral Neuromodulation", Neurology and Urodynamics 36:486-489 (2017).

Oerlemans, D.J. et al. Abstract of "Is On-Demand Sacral Neuromodulation in Patients with OAB Syndrome a Feasible Therapy Regime?", Neurourol Urodun 2011:30:1493-1496.

* cited by examiner

METHOD AND USER INTERFACE FOR MANAGING DUTY-CYCLED ELECTRICAL NERVE STIMULATION

CROSS-REFERENCE TO RELATED APPLICATIONS

This application claims the benefit of U.S. Provisional Application Ser. No. 63/198,663, filed Nov. 2, 2020, the disclosure of which is hereby incorporated by reference in its entirety.

FIELD

The present technology is generally related to methods, systems and devices related to electrical stimulation therapy.

BACKGROUND

Overactive bladder syndrome is a condition where there is a frequent feeling of the need to urinate to a degree that it negatively affects a person's life. Overactive bladder syndrome is characterized by a group of four symptoms: urgency (e.g., a sudden, compelling desire to pass urine that is difficult to defer), urinary frequency (e.g., feeling the need to urinate more than eight times per day), nocturia (e.g., interrupted sleep caused by an urge to urinate), and urge incontinence (urinary incontinence characterized by the involuntary loss of urine occurring for no apparent reason while urinary urgency is experienced). As many as 30% of men and 40% of women in the United States live with overactive bladder syndrome; the economic cost associated with this disorder is estimated to be in the billions of dollars each year.

Unfortunately, it is often difficult to successfully treat overactive bladder syndrome through traditional behavioral methods, such as pelvic floor exercises and bladder training. Medications are typically no more effective than behavioral methods, and are often associated with negative side effects. More recently, various methods of electrical nerve stimulation have been developed. Two of the more promising treatment methods include sacral nerve stimulation therapy and tibial nerve stimulation therapy.

Sacral nerve stimulation therapy is a treatment that uses a small device to send mild electrical impulses to nerves located in the lower region of the spine (just above the tailbone). These nerves, referred to as sacral nerves (specifically S2, S3 and S4), influence the behavior of structures such as the bladder, sphincter and pelvic floor muscles. In some cases, electrical stimulation of the sacral nerves can successfully eliminate or reduce overactive bladder syndrome, as well as a host of other bodily disorders including urinary incontinence, urinary urge/frequency, urinary retention, pelvic pain, bowel dysfunction (constipation, diarrhea, etc.), and erectile dysfunction among others.

Tibial nerve stimulation therapy is similar to sacral nerve stimulation therapy, however instead of stimulation of the sacral nerves, the tibial nerves (e.g., acupoints SP6, KI7, and/or KI8) of the patient are electrically stimulated. By contrast to the sacral nerves, which are located at the base of the vertebral column, access to the tibial nerves can generally be gained at a shallow depth within the lower leg of a patient. Accordingly, although sacral nerve stimulation may be more effective for some patients, implantation of a tibial nerve stimulation device is considered less intrusive.

Historically and conventionally, electrical nerve stimulation (defined at a high level by stimulation pulse training characterized by amplitude, pulse width and rate), provided by implantable neurostimulation devices or neuromodulation devices is delivered continuously (e.g., without interruption). However, implantable systems have also offered the ability to duty cycle stimulation with user-defined "on" and "off" times. It is believed that duty cycling (e.g., cycling of the electrical nerve stimulation on and off) may be equally as effective in achieving therapeutic benefit for patients as continuous stimulation, with the added benefit of reducing energy usage and thereby extending battery life.

SUMMARY

The techniques of this disclosure generally relate to systems and methods for managing duty cycled electrical nerve stimulation. In some embodiments, the duty cycling can be used to fill the notion of a "prescribed therapy regimen," thereby enabling a user defined stimulation regimen for patients, or stimulation therapy can be provided at particular times or occurring within a desired window of time for a defined interval (e.g., stimulation therapy begins at 10 PM and turns off at 6 AM, Monday through Friday, but shifts to 11 PM to 7 AM Saturday through Sunday). Accordingly, in some embodiments, the user can specify an exact dosing schedule that may vary from day-to-day. Further, some embodiments enable the patient to "pause" or temporarily turn the therapy off within a prescribed duty cycle. Moreover, some embodiments of the present disclosure enable duty cycle tracking to compare the electrical nerve stimulation actually delivered to the patient to the clinician prescribed therapeutic regimen.

Historically, implementation of cycling on implantable neurostimulation devices requires manual user intervention. For example, conventional methods of the cycling of a cadence of nerve stimulation are affected by either manually turning the therapy on or off, or modifying the amplitude of the therapy beyond what was originally prescribed. Such manual overriding operations are typically considered disruptive of the regular or prescribed stimulation regimen, which can result in the delivery of a less than desirable amount of neurostimulation, or therapy beyond what was intended to be provided, resulting in an increase in energy usage by the implantable device with little to no therapeutic benefit. Embodiments of the present disclosure mitigate these issues through additional functionality configured to enable greater utility for cycling relative to a prescribed therapy in a manner which builds upon or augments the existing notion of duty cycling within neuromodulation systems.

In some embodiments, the disclosed systems and methods can be configured to enable a clinician or other user, through the use of an external programming device, to specify an exact start time and date of the first therapy dose (e.g., a first cycle on period), thereby relieving the subject of the nerve stimulation of any further action in order to receive the prescribed therapy at the desired time. Additionally, in some embodiments, a user interface can be provided to enable users to specify an exact dosing schedule (e.g., in a "calendar view" format), thereby enabling a therapy regimen to be defined (e.g., both the interval between therapy sessions and the duration of the therapy). In some embodiments, the user interface can further enable specific therapy regimens to be delivered on specific days. For example, in some embodiments, doses of a therapy regimen can be scheduled around times when the delivery of neurostimulation therapy is not desired (e.g., when driving, etc.). In another example, the therapy regimens can be programmed to decrease in amplitude over a period of days or weeks in anticipation of the patient's condition improving (e.g., where therapeutic benefit can be achieved at lower power settings), which can extend device longevity.

In some embodiments, the disclosed systems and methods can be configured to enable "pausing" of the therapy, thereby enabling patients to temporarily discontinue a particular therapy session in a manner that does not disrupt the prescribed or regularly scheduled therapeutic regimen. In some embodiments, pausing therapy can be accomplished by decoupling therapy changes from cycling, so that the neurostimulation device is able to track cycling on/off independently from therapy on/off actions. Similarly, changes to stimulation parameters (e.g., amplitude, pulse width, rate, etc.) can be decoupled from cycling, so that such changes do not automatically restart the cycling interval (or immediately start a new cycle interval following a paused or "off" period).

In some embodiments, the disclosed systems and methods can be configured to enable tracking, via the implantable neurostimulation device or software on an external programmer, thereby enabling the tracking of delivered neurostimulation therapy. Thereafter, the neurostimulation therapy actually delivered to the patient can be compared to the prescribed or originally programmed therapy regimen. By tracking this information, additional stimulation can be automatically delivered (or not delivered) to compensate for any missed (or excessive) therapy doses within the overall therapy regimen. Tracking in comparison can also enable automatic adjustments of, for example, amplitude, pulse width, rate, etc., back to a prescribed or originally programmed therapy regimen for the purpose of inhibiting excessive drift or deviation from the original intended therapy.

One embodiment of the present disclosure provides an implantable neurostimulation system having an implantable neurostimulation device having one or more electrodes configured to deliver electrical energy to a patient according to a prescribed dosing pattern for the treatment of one or more physiological conditions, and an external programmer configured to wirelessly communicate with the implantable neurostimulation device, wherein the external programmer includes a user interface enabling a clinician to define an irregular dosing pattern, wherein a dose pattern during each day of a calendar month is individually programmable.

In one embodiment, the implantable neurostimulation device is at least one of a neuromodulation system adapted for sacral nerve stimulation or a neuromodulation system adapted for tibial nerve stimulation. In one embodiment, the external programmer is at least one of a mobile computing device, desktop computer or dedicated implantable neurostimulation device programmer. In one embodiment, a timing of the clinician defined dosing pattern is executed by a real-time clock embedded within the implantable neurostimulation device. In one embodiment, the implantable neurostimulation system further includes a patient controlled external programmer. In one embodiment, the patient controlled external programmer enables the delivered electrical energy to be selectively paused without permanent modification of the clinician defined dosing pattern. In one embodiment, the patient controlled external programmer enables an amplitude of the delivered electrical energy to be selectively adjusted without permanent modification of the clinician defined dosing pattern. In one embodiment, the implantable neurostimulation device is configured to compare the delivered electrical energy to the clinician defined dosing pattern. In one embodiment, the implantable neurostimulation device is configured to transmit information regarding the delivered electrical energy to the external programmer, and the external programmer is configured to compare the delivered electrical energy to the clinician defined dosing pattern.

Another embodiment of the present disclosure provides an implantable neurostimulation system including an implantable neurostimulation device having one or more electrodes configured to deliver electrical energy to a patient according to a prescribed dosing pattern for the treatment of one or more physiological conditions, and a patient external programmer configured to wirelessly communicate with the implantable neurostimulation device, the patient controlled external programmer enabling at least one of the delivered electrical energy to be selectively paused or an amplitude of the delivered electrical energy to be selectively adjusted without permanent modification of the prescribed dosing pattern.

Yet another embodiment of the present disclosure provides an implantable neurostimulation system including an implantable neurostimulation device having one or more electrodes configured to deliver electrical energy to a patient according to a prescribed dosing pattern for the treatment of one or more physiological conditions, and an external programmer configured to wirelessly communicate with the implantable neurostimulation device, wherein the external programmer includes a user interface configured to display a comparison between the electrical energy actually delivered to the patient and the prescribed dosing pattern.

The details of one or more aspects of the disclosure are set forth in the accompanying drawings and the description below. Other features, objects, and advantages of the techniques described in this disclosure will be apparent from the description in the drawings, and from the claims.

BRIEF DESCRIPTION OF THE DRAWINGS

The disclosure can be more completely understood in consideration of the following detailed description of various embodiments of the disclosure, in connection with the accompanying drawings, in which.

While embodiments of the disclosure are amenable to various modifications and alternative forms, specifics thereof shown by way of example in the drawings will be described in detail. It should be understood, however, that the intention is not to limit the disclosure to the particular embodiments described. On the contrary, the intention is to cover all modifications, equivalents, and alternatives falling within the spirit and scope of the subject matter as defined by the claims.

DETAILED DESCRIPTION

Various example embodiments of neuromodulation or neurostimulation devices and systems are described herein for managing duty cycled electrical nerve stimulation delivered to a subject. Although specific examples of sacral and tibial neuromodulation are provided, it is to be appreciated that the concepts disclosed herein are extendable to other types of neurostimulation devices. Further, while the treatment of overactive bladder syndrome is provided as one example therapy regimen, embodiments of the present disclosure can be used to treat a host of other bodily disorders including, but not limited to, urinary incontinence, urinary urge/frequency, urinary retention, pelvic pain, bowel dysfunction (constipation, diarrhea, etc.), and erectile dysfunction among others. It also to be appreciated that the term "clinician" refers to any individual that can prescribe and/or program neuromodulation with any of the example embodiments described herein or alternative combinations thereof. Similarly, the term "patient" or "subject," as used herein, is to be understood to refer to an individual or object in which the neuromodulation therapy is to occur, whether human, animal, or inanimate. Various descriptions are made herein, for the sake of convenience, with respect to the procedures being performed by a clinician on a patient or subject (the involved parties collectively referred to as a "user" or "users") while the disclosure is not limited in this respect.

Figure 1A:
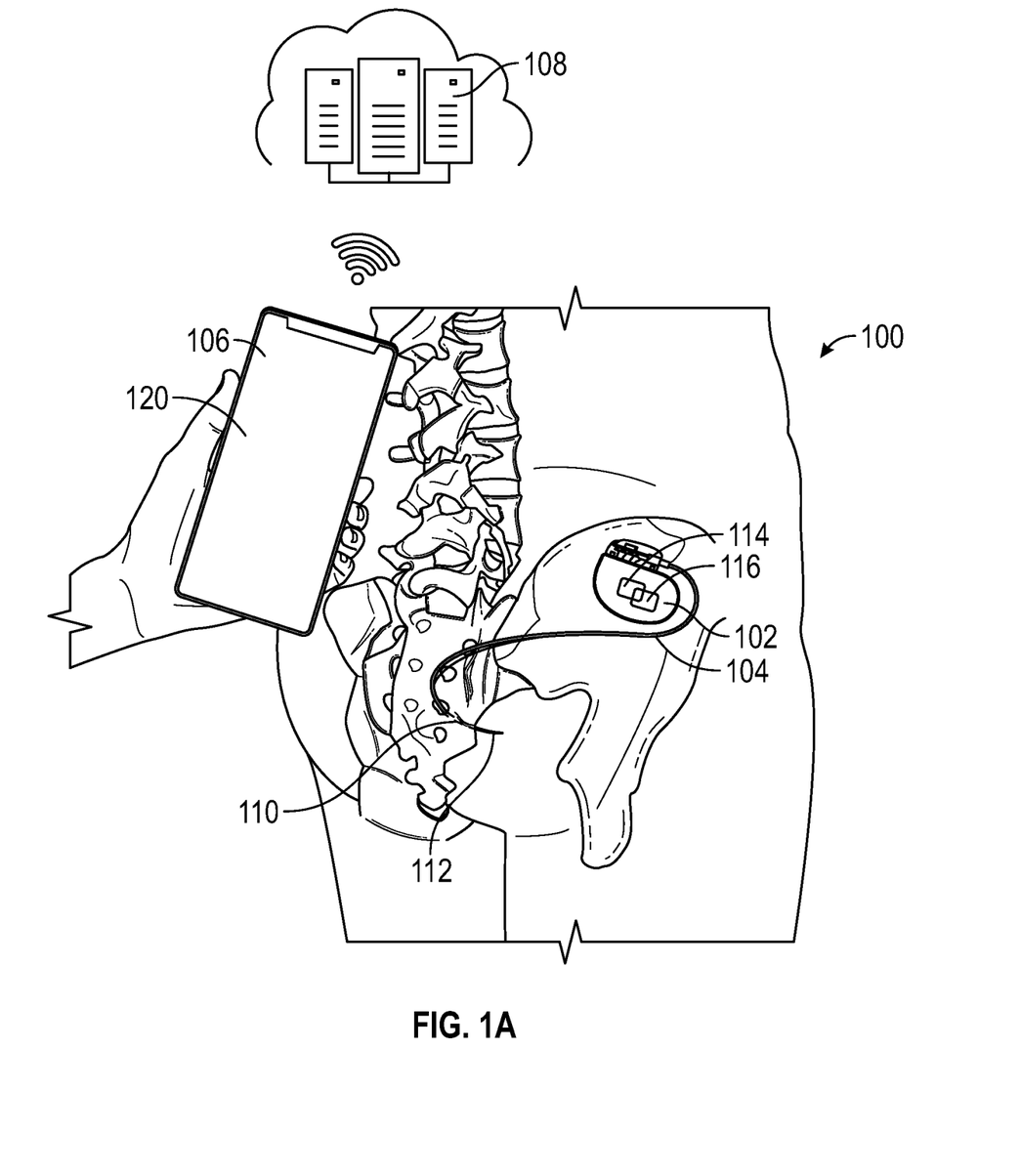
FIG. 1A is a schematic view depicting an implanted neuromodulation system adapted for sacral nerve stimulation, in accordance an embodiment of the disclosure.

FIG. 1A schematically illustrates an example of a neuromodulation system 100 adapted for sacral nerve stimulation. Neuromodulation system 100 includes a neurostimulator device 102 implanted in a lower buttock region of a patient, connected to an implanted stimulation lead 104 extending through a foramen for stimulation of a sacral nerve. The stimulation lead 104 can have a variety of shapes, can be a variety of sizes, and can be made of a variety of materials, which size, shape, and materials can be tailored to the specific treatment application. The electrical pulses generated by the neuromodulation system 100 are delivered via one or more stimulation electrodes 112 at or near a distal portion 110 of the stimulation lead 104. The pulsed electrical stimulation may be to one of several nerves; however for purposes of describing the system 100, the stimulation site is referred to herein simply as "sacral nerves." It should be understood that the term "sacral nerves" as used herein includes sacral nerves S1, S2, S3, S4, as well as other nerve sites such as the pudendal nerve, superior gluteal nerve, lumbo-sacral trunk, inferior gluteal nerve, common fibular nerve, tibial nerve, posterior femoral cutaneous nerve, sciatic nerve, and obturator nerve. Additionally, stimulation may be provided unilaterally or bilaterally via two or more leads. In another embodiment, neurostimulator device 102 may be leadless, having one or more electrodes on or otherwise coupled to a housing of neurostimulator device 102.

Figure 1B:
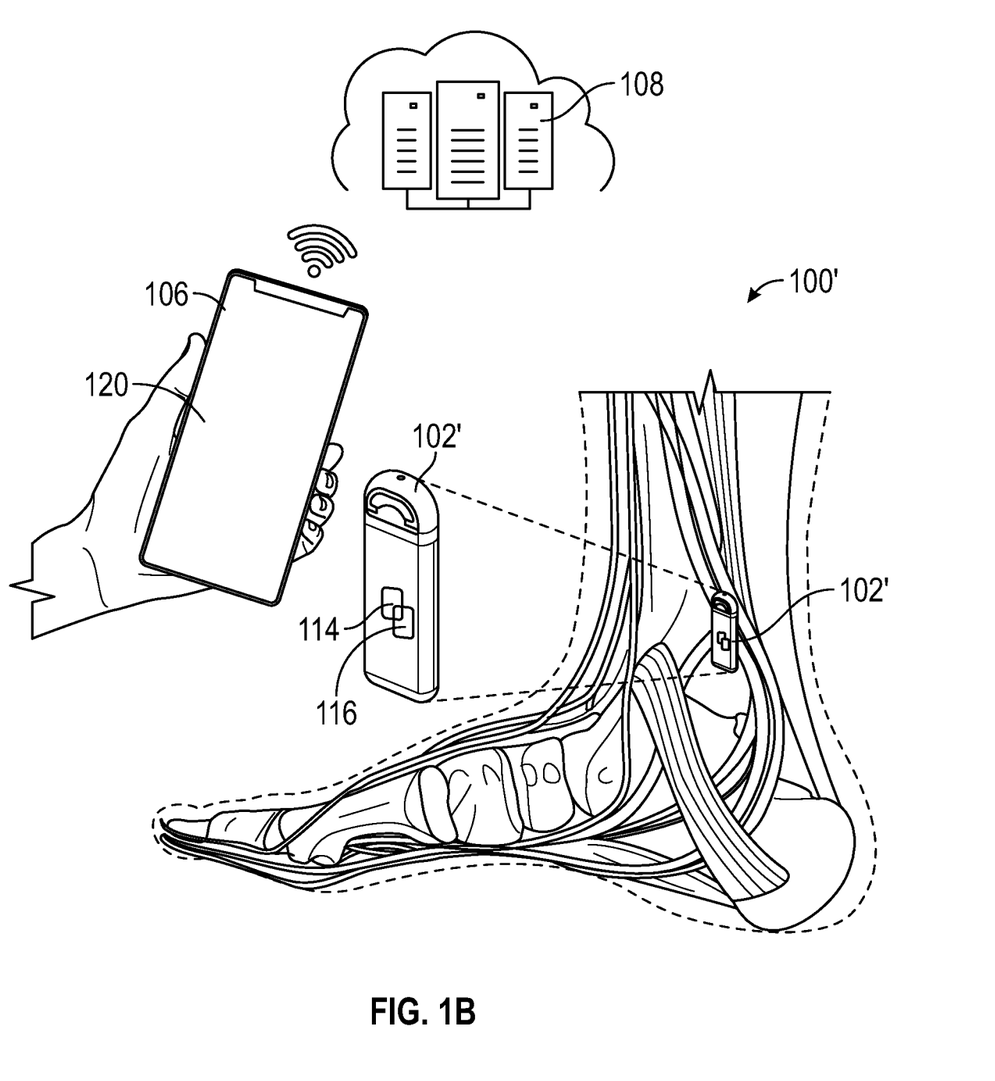
FIG. 1B is a schematic view depicting an implanted neuromodulation system adapted for tibial nerve stimulation, in accordance an embodiment of the disclosure.

FIG. 1B schematically illustrates an example of an implanted neuromodulation system 100' adapted for tibial nerve stimulation. Neuromodulation system 100' includes a neurostimulator device 102' implanted in a leg of a patient near the ankle adjacent to the tibial nerve. In some embodiments, the neurostimulator device 102' can be implanted under the skin and cutaneous fat layer via a small incision (e.g., about one to three cm) above the tibial nerve on the medial aspect of the patient's ankle. In some embodiments, the neurostimulator device 102' can be positioned adjacent to the region defined by the flexor digitorum longus, flexor halluces longus, and soleus in which the tibial nerve is contained, and implanted adjacent to and proximal to a facia layer. In some embodiments, neurostimulator device 102' can be a leadless device, in which a primary and a secondary electrode of the neurostimulator device 102' are configured to face towards the tibial nerve upon implantation. In other embodiments, neurostimulator device 102' can include a lead with a stimulation electrode thereon, configured to be implanted near a tibial nerve.

Each of neurostimulator devices 102, 102' can include circuitry for generating and delivering neurostimulation pulses, enclosed in a sealed housing and coupled to one or more therapy delivery electrodes, control circuitry for operating the neurostimulator device, communication (telemetry) circuitry and associated components, and a power source for providing power for generating and delivering stimulation pulses and powering other device functions. In embodiments, the power source may comprise a primary battery cell, a rechargeable battery cell, or an inductively coupled power source.

With reference to both FIGS. 1-B, in some embodiments, the neuromodulation system 100, 100' can further include an external programmer 106 configured to wirelessly communicate with both the neurostimulator device 102, 102' and an external server 108. For example, in some embodiments, the external programmer 106 can be configured to transmit programming data or instructions to a processor 114, 114' of the neurostimulator device 102, 102', which can in turn be saved in a memory 116, 116' of the neurostimulator device 102, 102'. In some embodiments, the neurostimulator device 102, 102' can include a real-time clock 118 (as depicted in FIGS. 3 & 5) for execution of the transmitted programming data. In some embodiments, the external programmer 106 can be configured to receive data (e.g., therapeutic delivery data, efficacy data, etc.) from the neurostimulator device 102, 102'. Although the external programming device 106 is depicted as a mobile computing platform (e.g., cellular telephone), other types of external programming devices, such as a desktop computer, tablet, smart watch or other wearable device, or dedicated programming platform are also contemplated. In some embodiments, the external programming device 106 may alternatively be referred to as at least one of a "clinician programmer" or "patient programmer."

In some embodiments, data communicated between the external programming device 106 and neurostimulator device 102, 102' can be transmitted to the external server 108 for wider dissemination, analysis and longer-term storage. In some embodiments, the external server 108 can be configured as a network of servers and/or a computing cloud. For example, in some embodiments, the external server 108 can include one or more complex algorithms representing machine learning and/or a neural network configured to process and analyze neurostimulator device 102, 102' data in an effort to further improve patient outcomes.

Figure 2:
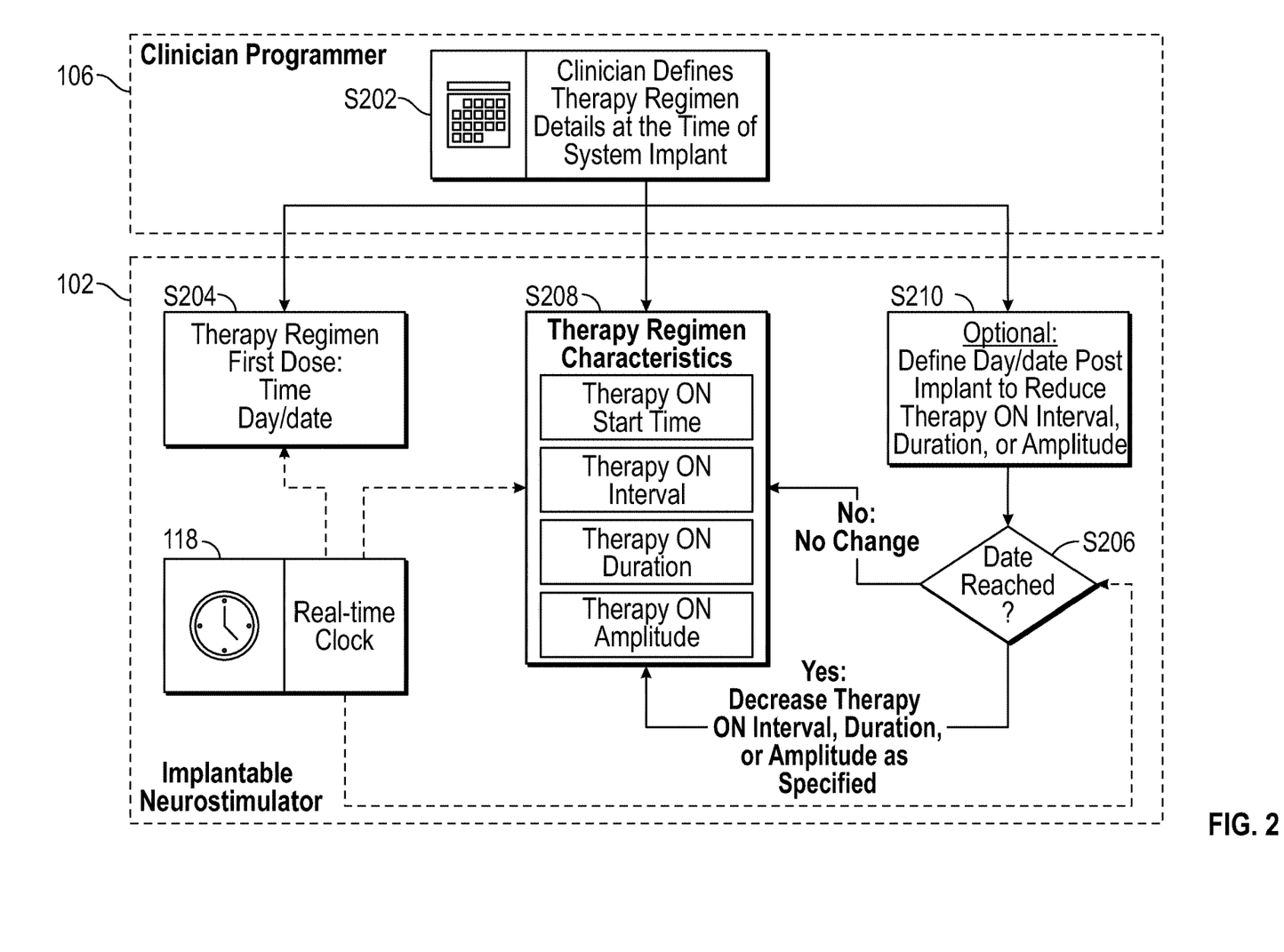
FIG. 2 is a flowchart depicting a method of programming a dosing schedule, in accordance with an embodiment of the disclosure

With reference to FIG. 2, a flowchart depicting a method 200 of programming a dosing schedule is depicted in accordance with an embodiment of the disclosure. For example, in one embodiment, a user (through an external programming device 106) can specify an exact start time and date of the first therapy dose (e.g., the first cycle "on" period of a prescribed therapeutic regimen), thereby alleviating the patient of the need to take further action for the prescribed therapy to begin at a desired date/time. According to such a method, at S202, a clinician or other user can define the therapy regimen details (e.g., start time and date of the first therapy dose). The therapy regimen details can be defined at the time that the neurostimulator device 102, 102' is implanted, or any other time that a new therapy regimen is prescribed. At S204, the therapy regimen details can be communicated to the neurostimulator device 102, 102'. At S206, any date/time associated with the therapy regimen details can be compared to a real-time clock 118 (which can be a part of processor 114). Upon reaching the start time and date of the first therapy dose, the prescribed neurostimulation therapy can commence.

As further depicted in FIG. 2, in another embodiment, the external programming device 106 can present a user interface 120 (as depicted in FIGS. 1A-B) configured to enable a user to specify a nonrepeating, irregular dosing pattern, for example in a calendar view where each day in any given week can be programmed with a different therapeutic regimen. According to such a method, at S202, a clinician or other user can define the therapy regimen details (e.g., the neurostimulation therapy start time, interval, duration, amplitude, etc. for each day of a displayed calendar). At S204, the therapy regimen details can be communicated to the neurostimulator device 102, 102'. Thereafter, any date/time associated with the therapy regimen details can be compared to a real-time clock 118 for execution of neurostimulation therapy according to the therapy regimen details, thereby enabling date specific neurostimulation programming. Accordingly, in some embodiments the method 200 enables a user to program neurostimulation to occur (or not occur) at a specific time or window of time within a given day of a calendar month, week or other prescribed period of time. For example, a user may elect to avoid neurostimulation during normal working hours or in anticipation of driving. In another example, a user may find that the neurostimulation therapy is most effective when delivered at a particular time of the day (e.g., completion of neurostimulation therapy just prior to beginning their morning work shift) which may vary from day-to-day, necessitating an irregular therapy regimen schedule.

As further depicted in FIG. 2, in yet another embodiment, method 200 can enable a user to establish a date to commence a relative decrease in amplitude (or other therapeutic parameters) (e.g., when it is anticipated that a therapeutic benefit can be achieved at lower power settings). For example, a clinician or other user may desire for therapy to be delivered at a first amplitude or at a first frequency for an initial time period after implantation (e.g., one to three months), then switch to a second, lower amplitude or second, lower frequency after expiration of the initial time period. According to such a method, at S202, a clinician or other user can define the therapy regimen details (e.g., the date at which a decrease in amplitude or other therapeutic parameters is to commence). At S204, the therapy regimen details can be communicated to the neurostimulator device 102, 102'. Thereafter, any date/time associated with the therapy regimen details can be compared to a real-time clock 118 for execution of neurostimulation therapy according to the therapy regimen details, thereby enabling an automated deescalation of the delivered neurostimulation programming where therapeutic benefit is still achieved but at lower power settings, thereby also helping to extend device (e.g., battery life) longevity.

Figure 3A:
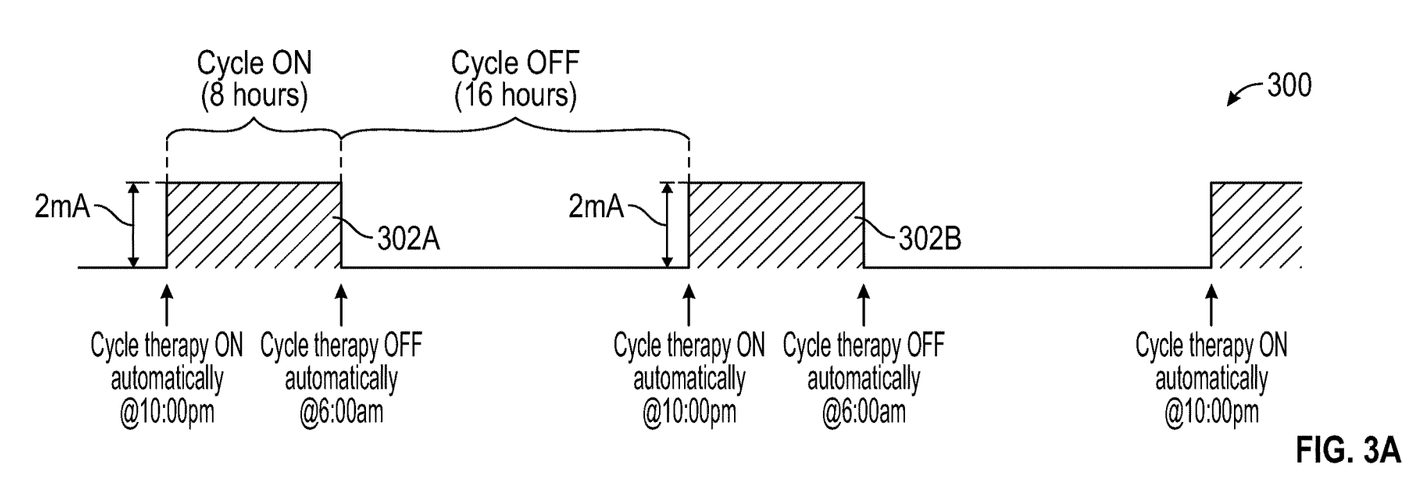
FIG. 3A is a graphical representation of a partial therapeutic regimen, in accordance with a first embodiment of the disclosure.

With reference to FIG. 3A a graphical representation of a partial therapeutic regimen 300 is depicted in accordance with an embodiment of the disclosure. According to the partial therapeutic regimen 300, a first dose of electrical neurostimulation 302A is configured to automatically commence at 10 PM for a duration of eight hours with an amplitude of 2 mA. Thereafter, no electrical neurostimulation is scheduled to take place for a period of 16 hours. A subsequent dose of electrical neurostimulation 302B is automatically set to commence at 10 PM within the following 24-hr period for the same duration and amplitude. In some embodiments, the disclosed systems and methods can be configured to enable a user to "pause" the therapy, thereby enabling patients to temporarily discontinue neurostimulation therapy in a manner that does not disrupt the prescribed or regularly scheduled therapeutic regimen.

Figure 3B:
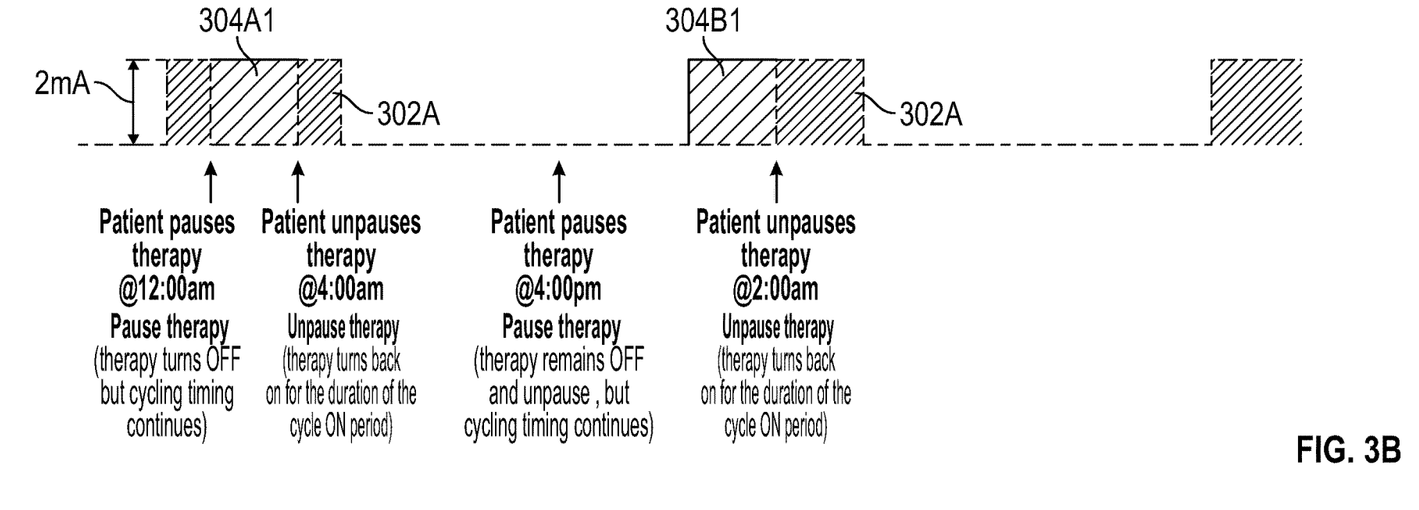
FIG. 3B is a graphical representation of a partial therapeutic regimen, in accordance with a second embodiment of the disclosure.

For example, with reference to FIG. 3B a graphical representation of initiating a pause 304A1 within a therapeutic regimen is depicted in accordance with an embodiment of the disclosure. In particular, FIG. 3B depicts a user pausing the electrical neural stimulation at 12 AM (during the first dose of electrical neurostimulation 302A), and un-pausing the electrical neural stimulation at 4 AM, thereby enabling the remaining first dose of electrical neural stimulation 302A to resume. A second pause 304B1 is initiated at 4 PM and removed or un-paused at 2 AM, during the second dose of electrical neurostimulation 302B. Accordingly, in some embodiments, through the use of a real-time clock 118, the neurostimulator device 102, 102' is able to maintain the prescribed therapy regimen while enabling the patient to "override" the regimen by selectively pausing therapy delivery (e.g., to avoid pain, discomfort, or when undertaking tasks where no neurostimulation therapy is desired).

Figure 3C:
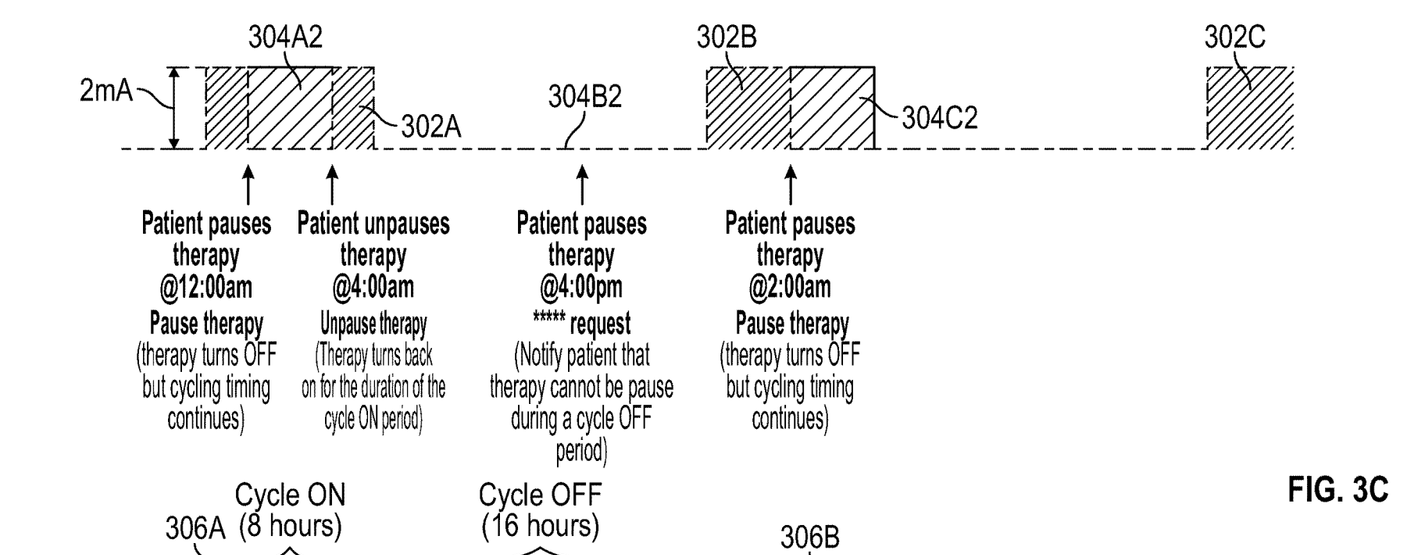
FIG. 3C is a graphical representation of a partial therapeutic regimen, in accordance with a third embodiment of the disclosure.

With reference to FIG. 3C, in another example embodiment, a user initiates a first pause 304A2 at 12 AM (during the first dose of electrical neural stimulation 302A), and un-pauses the electrical neural stimulation at 4 AM, thereby enabling the remaining first dose of electrical neural stimulation 302A to resume. A second pause 304B2 is initiated at 4 PM; however, unlike the example depicted in FIG. 3B, this pause request is ignored by the neurostimulator device 102, 102', as the pause 304B2 is not initiated during a scheduled dose of electrical neurostimulation. A third pause 304C2 is initiated at 2 AM during the second dose of electrical neurostimulation 302B. The third pause 304C2 continues until the end of the scheduled electrical neural stimulation 302B, at which point the pause 304C2 is automatically discontinued. A subsequent dose of electrical neurostimulation 302C commences at its regular scheduled time of 10 PM the next day for the same duration and amplitude. Accordingly, by decoupling therapy changes (e.g., pausing, unpausing, etc.) from the prescribed or scheduled cycling, the neurostimulator device 102, 102' is able to maintain a higher level of consistency in electrical neurostimulation delivery, while still enabling a user to interrupt electrical neurostimulation when desired (e.g., when experiencing pain or discomfort, while driving, etc.).

Figure 3D:
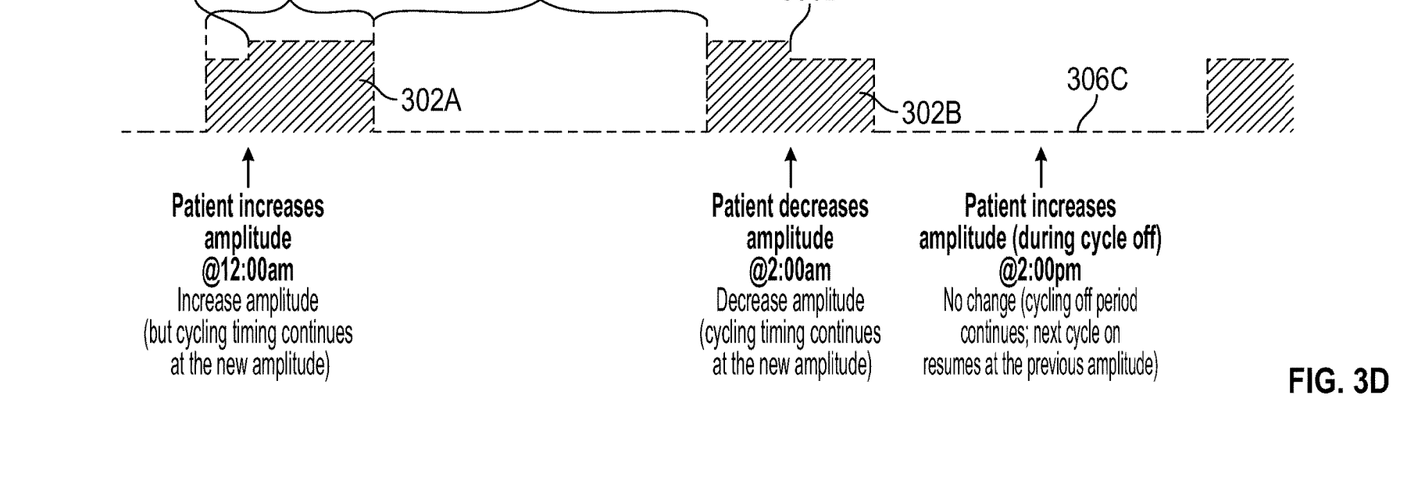
FIG. 3D is a graphical representation of a partial therapeutic regimen, in accordance with a fourth embodiment of the disclosure.

With reference to FIG. 3D, in another example embodiment, a user can selectively modify an amplitude of any given dose of electrical neurostimulation. For example, as depicted in FIG. 3D, a user sends a signal 306A to increase the amplitude at 12 AM (during the first dose of electrical neural stimulation 302A). In some embodiments, any modifications to amplitude can remain in effect for subsequent doses of electrical neurostimulation. In other embodiments, the amplitude can revert back to the prescribed amplitude upon the completion of any dose of electrical neural stimulation. Alternatively, the user can send a signal 306B to decrease the amplitude, which can have the effect of stepping down the amplitude of any given dose of electrical neurostimulation. In some embodiments, amplitude adjustments or modifications outside of the period of time when a dose of electrical neurostimulation is being administered can be ignored. Variations of the above identified modifications to a prescribed neurostimulation therapy are also contemplated.

Figure 4:
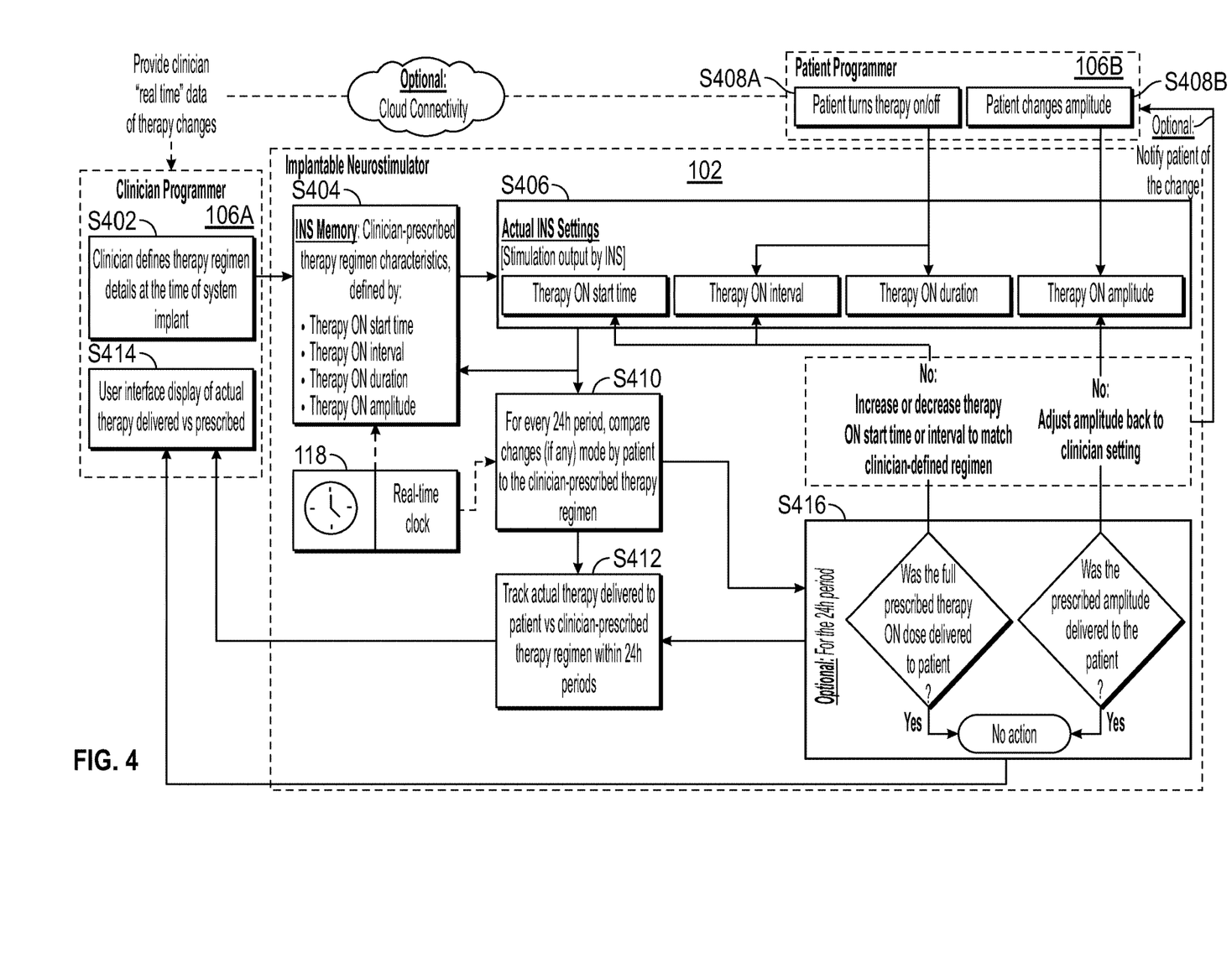
FIG. 4 is a flowchart depicting a method of electrical neurostimulation therapy delivery, in accordance with an embodiment of the disclosure.

With reference to FIG. 4, a flowchart depicting a method 400 of electrical neurostimulation therapy delivery tracking is depicted in accordance with an embodiment of the disclosure. For example, in one embodiment, the neurostimulation therapy actually delivered to the patient can be compared to the prescribed or originally programmed therapy regimen. Thereafter, additional stimulation can be automatically delivered (or not delivered) to compensate for any missed (or excessive) therapy doses within the overall therapy regimen. Comparative analysis (e.g., between actual delivered and prescribed neurostimulation therapy) can also enable automatic adjustments of, for example, amplitude, pulse width, rate, etc., back to a prescribed or originally programmed therapy regimen for the purpose of inhibiting excessive drift or deviation from the original intended therapy.

According to such a method, at S402, a clinician or other user can define the therapy regimen details (e.g., start time, interval, duration, and amplitude of a prescribed neurostimulation therapy), via clinician programmer 106A. For example, the therapy regimen details can be defined at the time that the neurostimulator device 102, 102' is implanted, or any other time that a new therapy regimen is prescribed. At S404, the therapy regimen details can be communicated to the neurostimulator device 102, 102'. Thereafter, the therapy regimen details can be executed as metered by the real-time clock 118. At S406, data representing the actual electrical stimulation output by the neurostimulator device 102, 102' (e.g., start time, interval, duration, amplitude, etc.) can be recorded. As previously disclosed, at S408A-B, a patient can selectively modify the therapy regimen (e.g., by pausing the therapy regimen, changing and amplitude of the therapy regimen, etc.).

At S410, a comparison of the data representing the actual electrical stimulation output by the neurostimulator device 102, 102' (recorded at S406) can be compared to data representing the prescribed electrical stimulation (recorded at S404) from time to time or on a periodic basis (e.g., every 24 hrs). At S412, a summary of the comparative analysis completed at S410 can be communicated to the external programming device 106A. At S414, a user interface of the external programming device 106A can graphically depict the graphical summary of the comparison between the actual and prescribed neurostimulation therapy. In other embodiments, S410 may be performed by clinician programmer 106A. The implanted neurostimulator device 102, 102' may transmit to clinician programmer 106A information representing the actual electrical stimulation output by the neurostimulator device 102, 102'.

At S416, automatic adjustments of the deliverable neurostimulation therapy can be made to compensate for deviations between the actual and prescribed neurostimulation therapy. For example, if it is determined that therapy was paused during the time that the prescribed neurostimulation therapy was scheduled to take place, the duration of a subsequent neurostimulation therapy can be increased and/or the interval between the previous neurostimulation therapy and the subsequent neurostimulation therapy can be decreased, such that the total duration of the actual delivered neurostimulation therapy meets the prescribed therapeutic regimen. In another example, if it is determined that the amplitude of the actual delivered neurostimulation therapy was altered, the amplitude of a subsequent neurostimulation therapy dose can be adjusted to meet the prescribed therapeutic regimen.

In embodiments if the full prescribed therapy ON dose was not delivered to the patient at operation S416, the patient programmer 106B can optionally be notified of an increase or decrease in therapy ON start time or interval to match a clinician-defined regimen. Similarly, in embodiments if the prescribed amplitude was not delivered to the patient at operation S416, the patient programmer 106B can optionally be notified the amplitude was adjusted back to clinician setting.

In embodiments, patient programmer 106B can optionally be connected to a network, such that patient programmer 106B is configured for cloud connectivity. Patient programmer 106B can communicate in a singular "cloud" or network or spread among many clouds or networks. In embodiments such cloud connectivity can enable patient programmer 106B to provide a clinician with "real time" data of therapy changes.

It should be understood that the individual steps used in the methods of the present teachings may be performed in any order and/or simultaneously, as long as the teaching remains operable. Furthermore, it should be understood that the apparatus and methods of the present teachings can include any number, or all, of the described embodiments, as long as the teaching remains operable.

In one embodiment, the neuromodulation system 100 can utilize one or more advanced algorithms, for example via a deep learning algorithm (e.g., an artificial neural network, or the like), in an effort to further improve patient outcomes. For example, in some embodiments, neuromodulation system 100 can be configured to conduct a series of experiments in neurostimulation therapy with a goal of improving the therapeutic effect of the neurostimulation therapy.

Figures 5A, 5B:
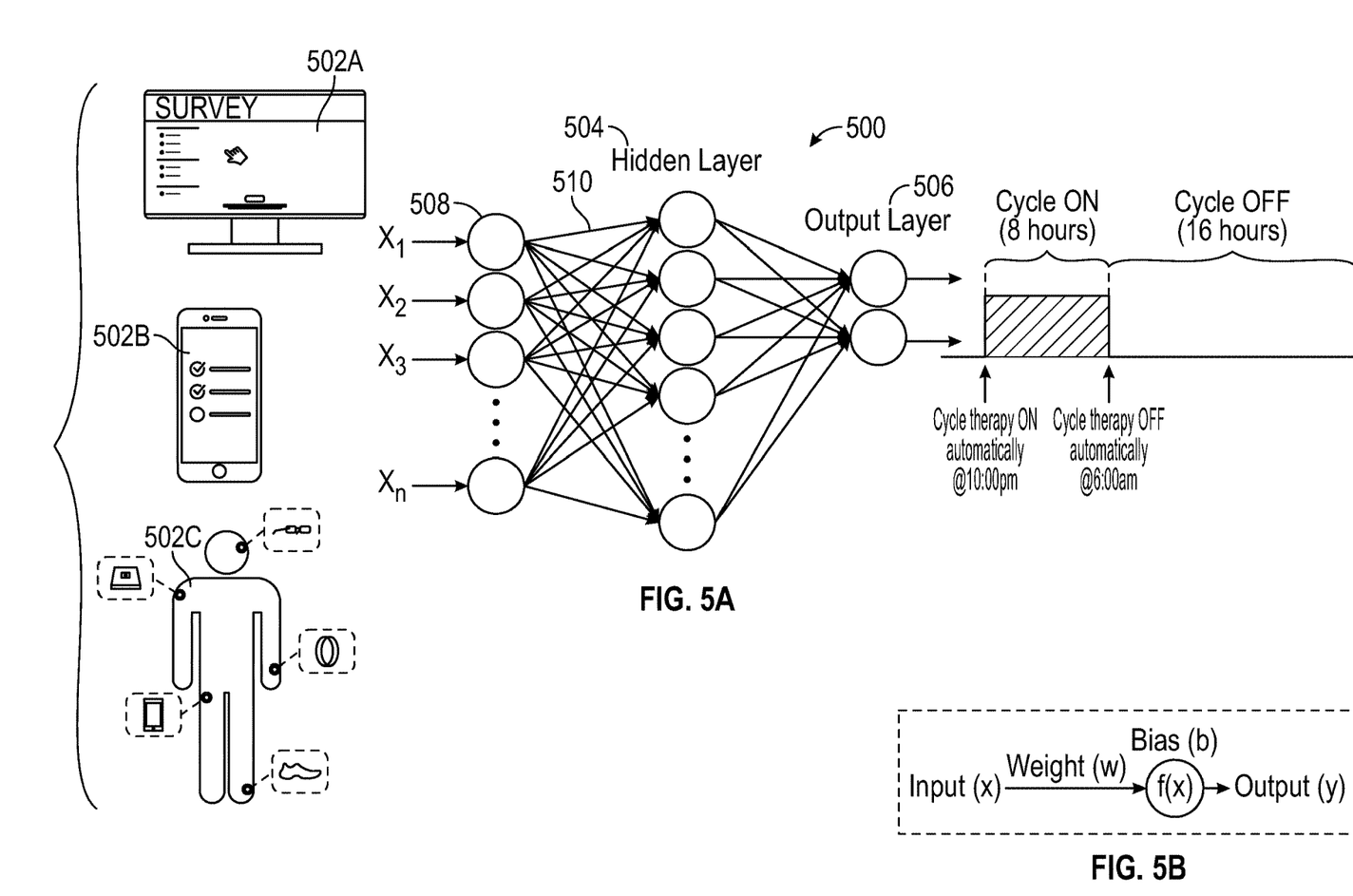
FIG. 5A is a diagram depicting a neural network, in accordance with an embodiment of the disclosure.
FIG. 5B depicts a single neuron within the neural network of FIG. 5A, in accordance with an embodiment of the disclosure.

For example, with reference to FIG. 5A, in one embodiment, the neural network 500, can include an input layer 502, one or more hidden layers 504, and an output layer 506. Each of the layers 502, 504, and 506 can include a corresponding plurality of neurons 508. Although only a single hidden layer 504 is depicted, it is contemplated that the neural network 500 can include multiple hidden layers 504.

The inputs for the input layer 502 can be a number between 0 and 1. Inputs to the neural network can include programming limitations and restrictions (e.g., designated windows of time when neurostimulation therapy should or should not occur, maximum durations, maximum amplitudes, etc.) (as depicted in FIG. 2), patient controlled pausing and amplitude modifications (as depicted in FIG. 3B-D), data feedback from comparisons between actual delivered and prescribed neurostimulation therapy (as depicted in FIG. 4), clinician feedback via one or more questionnaires 502A (e.g., presented on a clinician programmer 106A), patient feedback via one or more questionnaires 502B (e.g., presented on a patient programmer 106B), and/or feedback via one or more wearable sensors 502C (e.g., moisture probe, pressure sensor, heart rate monitor, pulse oximeter, accelerometer, etc.), wherein each of the input values for each of the inputs is scaled to a value of between 0 and 1.

Each of the neurons 508 in one layer (e.g., input layer 502) can be connected to each of the neurons 508 of the subsequent layer (e.g., hidden layer 504) via a connection 510, as such, the layers of the network can be said to be fully connected. Although it is also contemplated that the algorithm can be organized as a convolutional neural network, wherein a distinct group of input layer 502 neurons (e.g., representing a local receptive field of input pixels) can couple to a single neuron in a hidden layer 504 via a shared weighted value.

With additional reference to FIG. 5B, each of the neurons 508 can be configured to receive one or more input values (x) and compute an output value (y). In fully connected networks, each of the neurons 508 can be assigned a bias value (b), and each of the connections 510 can be assigned a weight value (w). Collectively the weights and biases can be tuned as the neural network 500 learns how to correctly classify the input values. Each of the neurons 508 can be configured as a mathematical function, such that an output of each neuron 508 is a function of the connection weights of the collective input, and the bias of the neuron 508, according to the following relationship:

$$y = w \cdot x + b$$

In some embodiments, output (y) of the neuron 508 can be configured to take on any value between 0 and 1. Further, in some embodiments the output of the neuron 508 can be computed according to one of a linear function, sigmoid function, tanh function, rectified linear unit, or other function configured to generally inhibit saturation (e.g., avoid extreme output values which tend to create instability in the network 500).

An output 506 of the neural network can be a programmed neural stimulation therapy regimen. In some embodiments, the output layer 506 can include neurons 508 corresponding to a desired number of outputs of the neural network 500. For example, in one embodiment, the neural network 500 can include a plurality of output neurons dividing a period of time (e.g., 24 hrs) into distinct increments, in which the likelihood of successful neural stimulation therapy can be indicated with an output value of between 0 and 1, such that the neural stimulation therapy regimen can be scheduled during the times where the likelihood of success is greatest, and conversely avoided where the likelihood of success is the least.

The goal of the deep learning algorithm is to tune the weights and balances of the neural network 500 until the inputs to the input layer 502 are properly mapped to the desired outputs of the output layer 506, thereby enabling the algorithm to accurately produce outputs (y) for previously unknown inputs (x). In some embodiments, the neural network 500 can rely on training data (e.g., inputs with known outputs) to properly tune the weights and balances.

In tuning the neural network 500, a cost function (e.g., a quadratic cost function, cross entropy cross function, etc.) can be used to establish how close the actual output data of the output layer 506 corresponds to the known outputs of the training data. Each time the neural network 500 runs through a full training data set can be referred to as one epoch. Progressively, over the course of several epochs, the weights and balances of the neural network 500 can be tuned to iteratively minimize the cost function.

Effective tuning of the neural network 500 can be established by computing a gradient descent of the cost function, with the goal of locating a global minimum in the cost function. In some embodiments, a backpropagation algorithm can be used to compute the gradient descent of the cost function. In particular, the backpropagation algorithm computes the partial derivative of the cost function with respect to any weight (w) or bias (b) in the network 500. As a result, the backpropagation algorithm serves as a way of keeping track of small perturbations to the weights and biases as they propagate through the network, reach the output, and affect the cost. In some embodiments, changes to the weights and balances can be limited to a learning rate to prevent overfitting of the neural network 500 (e.g., making changes to the respective weights and biases so large that the cost function overshoots the global minimum). For example, in some embodiments, the learning rate can be set between about 0.03 and about 10. Additionally, in some embodiments, various methods of regularization, such as L1 and L2 regularization, can be employed as an aid in minimizing the cost function.

Accordingly, in some embodiments, the neuromodulation system 100 be configured to utilize a variety of data as an input for the cloud computing platform 108 configured to operate a deep learning algorithm for the purpose of automatically scheduling neurostimulation therapy with a goal of tailoring the improving neurostimulation therapy specifically to maximize the therapeutic effect of the neurostimulation therapy.

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

In one or more examples, the described techniques may be implemented in hardware, software, firmware, or any combination thereof. If implemented in software, the functions may be stored as one or more instructions or code on a computer-readable medium and executed by a hardware-based processing unit. Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

What is claimed is:

1. An implantable neurostimulation device, comprising:
   a power source;
   a housing, including circuitry for generating neurostimulation therapy pulses;

one or more electrodes configured to deliver the neurostimulation therapy pulses to a patient; and telemetry components for communicating with an external programmer device, wherein the implantable neurostimulation device is configured to deliver a neurostimulation therapy to the patient according to a clinician prescribed dosing pattern comprising a plurality of therapy doses for the treatment of one or more physiological conditions, the plurality of therapy doses having an irregular pattern such that a therapy dose during each day of a calendar month is individually programmable, wherein the implantable neurostimulation device is configured to compare a delivered neurostimulation therapy in a first therapy dose to a prescribed first therapy dose, schedule an adjusted stimulation parameter for a second prescribed therapy dose based on any detected deviations between the first delivered and prescribed therapy doses, and automatically operate the neurostimulation device at the one or more adjusted stimulation parameters during the second prescribed therapy dose to deliver additional neurostimulation therapy pulses to compensate for the detected deviations between the delivered and prescribed first therapy doses, thereby fulfilling the prescribed dosing pattern.

2. The implantable neurostimulation device of claim 1, wherein the implantable neurostimulation device is at least one of neuromodulation device adapted for sacral nerve stimulation or a neuromodulation device adapted for tibial nerve stimulation.

3. The implantable neurostimulation device of claim 1, wherein the implantable neurostimulation device is configured to communicate with a mobile computing device, a desktop computer or a dedicated implantable neurostimulation device programmer.

4. The implantable neurostimulation device of claim 1, wherein delivery of the neurostimulation therapy according to the prescribed dosing pattern is executed by a real-time clock embedded within the implantable neurostimulation device.

5. The implantable neurostimulation device of claim 1, wherein the implantable neurostimulation device is configured to communicate with a patient controlled external programmer.

6. The implantable neurostimulation device of claim 5, wherein the implantable neurostimulation device is configured to selectively pause therapy delivery in response to a command received from the patient controlled external programmer, without permanent modification of the clinician defined dosing pattern.

7. The implantable neurostimulation device of claim 5, wherein the implantable neurostimulation device is configured to selectively adjust an amplitude of the therapy in response to a command received from the patient controlled external programmer, without permanent modification of the clinician defined dosing pattern.

8. The implantable neurostimulation device of claim 1, wherein the implantable neurostimulation device is configured to compare the delivered electrical energy to the clinician defined dosing pattern.

9. The implantable neurostimulation device of claim 1, wherein the stimulation parameters comprise either an amplitude, pulse width, or rate.

10. The implantable neurostimulation device of claim 1, wherein the stimulation parameters comprise either a start time, date, duration, or interval.

* * * * *